United States Patent
Aso et al.

(10) Patent No.: US 8,030,361 B2
(45) Date of Patent: Oct. 4, 2011

(54) CELL CULTURE CARRIER IMPLANTABLE IN VIVO

(75) Inventors: Yu Aso, Tokyo (JP); Makiko Kono, Tokyo (JP)

(73) Assignee: Koken Co., Ltd., Tokyo (JP)

( * ) Notice: Subject to any disclaimer, the term of this patent is extended or adjusted under 35 U.S.C. 154(b) by 474 days.

(21) Appl. No.: 12/064,011

(22) PCT Filed: Aug. 18, 2005

(86) PCT No.: PCT/JP2005/015378
§ 371 (c)(1),
(2), (4) Date: Feb. 25, 2008

(87) PCT Pub. No.: WO2007/020713
PCT Pub. Date: Feb. 22, 2007

(65) Prior Publication Data
US 2009/0156691 A1    Jun. 18, 2009

(51) Int. Cl.
*A61K 47/42* (2006.01)
*A61F 2/02* (2006.01)

(52) U.S. Cl. ..................... 514/773; 623/11.11
(58) Field of Classification Search ............ None
See application file for complete search history.

(56) References Cited

U.S. PATENT DOCUMENTS

| | | | | |
|---|---|---|---|---|
| 4,314,380 A * | 2/1982 | Miyata et al. | | 623/23.61 |
| 5,024,841 A * | 6/1991 | Chu et al. | | 424/422 |
| 5,731,417 A | 3/1998 | Swiderek et al. | | |
| 5,817,764 A * | 10/1998 | Swiderek et al. | | 530/356 |
| 5,830,493 A * | 11/1998 | Yokota et al. | | 424/426 |
| 6,350,274 B1 * | 2/2002 | Li | | 606/213 |
| 2004/0106550 A1 * | 6/2004 | Imaizumi | | 514/12 |
| 2005/0203611 A1 * | 9/2005 | Quax et al. | | 623/1.42 |

FOREIGN PATENT DOCUMENTS

| | | |
|---|---|---|
| JP | 06-022744 | 2/1994 |
| JP | 2003-093051 | 4/2003 |
| JP | 2005-040060 | 2/2005 |
| JP | 2005-130758 | 5/2005 |

* cited by examiner

*Primary Examiner* — Shanon A Foley
(74) *Attorney, Agent, or Firm* — Hahn & Voight PLLC; Roger C. Hahn

(57) ABSTRACT

A cell cultivation carrier implantable in vivo having independent pore with opening of 100 μm-1000 μm on the surface thereof produced by neutralization•gellation of collagen acidic solution, said collagen acidic solution is preliminary prepared by passing through a filter of 10 μm or less pore size by 5-20 mg/mL concentration. Especially, a cell cultivation carrier implantable in vivo having sufficiently self-organized accumulation shape•structure obtained by carrying out said neutralization under directionally supplying of alkali.

23 Claims, 1 Drawing Sheet

CELL CULTURE CARRIER IMPLANTABLE IN VIVO

FIELD OF THE INVENTION

Figure 1:
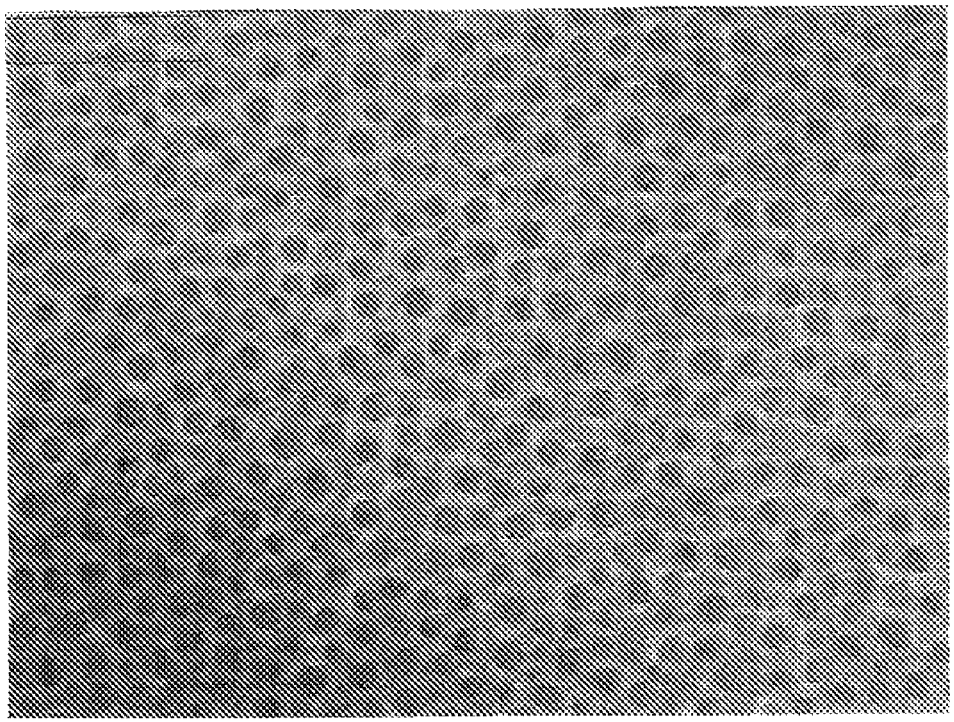

The present invention relates to a collagen carrier for cell cultivation which is implantable in vivo. In particular, the present invention relates to a culture carrier, which is usable for regenerative medicine and is possible to cultivate cells by high density, characterized by containing a cell to a collagen carrier having fine pores of uniform diameter and orientation.

BACKGROUND OF THE INVENTION

As a method for cultivation, there are several methods such as to cultivate by adhering a cell to a carrier or to cultivate a cell by floating in medium. In the case to culture a cell by adhering to a carrier, a material of carrier is an important factor to improve the usefulness for high density and efficient culture regenerative medicine.

As a material for a culture carrier, gelatin, cellulose, hydroxy apatite or collagen are known, however from the view point of practical use for regenerative medicine, it is desirable that a compound is easily absorbed in vivo after embedded. In the case of cellulose, it has a problem that it can not be absorbed in vivo, and from this point of view, collagen attracts attention. Further, as a material of carrier, it is necessary to be investigated from adhering ability of cell and efficiency, and collagen is attracted attention from this point of view.

As a shape of carrier, it is necessary to investigate from macroscopic view point such as stable preservative ability when the carrier is embedded in vivo, or from bioactivity view point such as adhering ability of cell, bioabsorption•effective bio tissue replacement are important factors. As a beads shape carrier, for example, a carrier of agarose beads to which collagen is coated is known, however, it has a problem that the holding of carrier to embedded part is difficult and abilities of absorbable•effective tissue replacement in vivo are not so good. In addition, as a carrier for adhering cell, micro carrier, hollow fiber, membrane or nonwoven cloth are known, and these subjects are improved from holding ability of carrier, however, is not sufficient from said bio activity view point.

In the meanwhile, in recent development of regenerative medicine, it becomes popular to use auto or allo cell or cell of other person for medical treatment. For example, cultivated skin or cultivated cartilage to which only epithelium cell in vitro cultivated or fibroblast cell in vitro that produces interstitial compound in vivo are introduced are developed and is the stage of practical use.

In these regenerative medicines, after cells are cultivated by suitable carrier, it is clearly understood that the use of a cultivated cell which can be put back in vivo together with the carrier is desirable.

Further, as a carrier having said desired characteristic for regenerative medicine, it is considered that such subject can be accomplished by combining a cell, a carrier for cell and an activated factor to promote effective cultivation of cell. For example, in a case of bone or cartilage transplantation, it is important that it further contains sufficiently a matrix component (interstitial compound), such as, apatite, collagen or mucopolysaccharide and others. Bone or cartilage is composed of apatite, collagen, mucopolysaccharide or others which is produced by cell, and as a transplantation fragment for these tissue, it is necessary to contain sufficient amount of matrix component and to have physical characteristics similar in vivo.

Furthermore, because it replaces with own tissue in vivo, matrix components become very important for the purpose to act as an excellent scaffold for cultivation of own cell. In such a requirement, a spongy carrier is proposed (JP62-502936 publication; WO86/05811, document 1), because a spongy carrier of collagen having average pore size of approximately 1 μm to 150 μm improves cultivation efficiency. And, the invention of transplantable transplantation fragment, comprising a carrier with stable three dimensional structure having inner pore which can pass through nutrient liquid and containing cell in it is proposed (JPH8-511679 publication; WO94/20151, document 2), invention of an implantable material produced from a polymer filament having good shape holding ability (JPH9-182784 publication, document 3), further, the invention of matrix for reproduction of cartilage tissue containing collagen II fiber that composes extraceller matrix having good reproduction ability of cartilage tissue when embedded in vivo (JPH11-503338 publication; WO96/25962, document 4) are proposed.

Further, as a collagen carrier for cell cultivation that can cultivate cells by high density and a method for production thereof, a method for production of cell cultivation collagen carrier comprising, having pore size controlled in 50-2000 μm range, said pore is penetrating straightly from one surface to another surface and forming collagen fibrils arranged straightly from one surface to another surface by exposing cell cultivation collagen in which each pores are substantially and independently existing, and by exposing acidic solution to ammonia gas, forming collagen fiber sequenced from one surface to another surface and simultaneously forms straight water pole from one surface to another surface, then evaporate water in gel by freeze dry method is proposed (Japanese Patent 3170693 registered on Mar. 23, 2001, published on May 28, 2001, document 5). And as the effect thereof, following point is mentioned. That is, pore size can be controlled by concentration of ammonia gas and collagen carrier having most suitable pore size and structure to a cell to be cultivated and said pores are controlled along with supplying direction of ammonia gas can be obtained, further surface area of it can be enhanced, therefore, a cell cultivation collagen carrier that can cultivate cells by high density.

Up to this time, an investigation of a carrier as a scaffold of cell was carried out, however, a report of real carrier for regenerative medicine aiming self accumulation of matrix component produced from one's own cell is not found out.

Further, as a factor for activation of cell to said regenerative medicine, factors such as BMP (Bone Morphogeneic Protein), β FGF (β fibroblast growth factor) are known, and recently, recombinant human these factors can use. Further, these factors can be extracted from animal's bone such as bovine and can be used. However, any kind of activation factor, it is important for formation of tissue based on said activation factor to maintain said activation factor by certain concentration at surrounding part.

Recently, big expectation is loaded on regenerative medicine, and development relating to regenerative medicine is becoming an important target, and many firms are joining to the development, however, desired carrier for regenerative medicine is not developed yet, and it is a realistic current problem.

The subject of the present invention is to provide a carrier characterizing, after adhering removed cell or tissue thereof to a carrier and cultivating said removed cell or tissue thereof, transforming the carrier to have figure•structure that is possible to be transplanted in vivo without anaplasia of cell and so as the matrix produced by cell to be accumulated sufficiently in own tissue.

For the purpose to dissolve said subject, the inventors of the present invention basically investigated collagen itself, and considered the development of collagen that can form a cell cultivation carrier, and said collagen can form a carrier having figure•structure possible to accumulate matrix sufficiently in own tissue in vivo, namely, collagen having fine pore structure of figure•structure controlled to thickness direction. Based on said consideration, many experiments were carried out by trial and error, and the inventors of the present invention found out that the neutralization-gellation can be more effectively advanced by controlling fine pore size and progressing direction, and, good effect can be accomplished by transforming soluble collagen to a collagen from which aggregated collagen is removed. For example, the inventors of the present invention found out that by progressing to thickness direction by controlling diffusion, a carrier having figure•structure characterizing that fine pores having uniform fine pore diameter are uniformly sequenced can be obtained, and in said figure•structure, matrix can be sufficiently accumulated in own tissue in vivo, and accomplished to dissolve above mentioned subject.

DISCLOSURE OF THE INVENTION

The $1^{st}$ one of the invention is (1) a cell cultivation carrier implantable in vivo having independent pores with opening of 100 μm-1000 μm on the surface thereof produced by neutralization•gellation of collagen acidic solution, said collagen acidic solution is preliminary prepared by passing through a filter of 10 μm or less pore size by 5-20 mg/mL concentration. Desirably, (2) is the cell cultivation carrier implantable in vivo of above mentioned (1) characterized by being freeze dried after neutralization•gellation, further, (3) is the cell cultivation carrier implantable in vivo of above mentioned (1) or (2) characterized to neutralize so as to have directionality at neutralization•gellation, or more desirably (4) is the cell cultivation carrier implantable in vivo of above mentioned (1), (2) or (3) characterizing to use basic gas at neutralization•gellation, still further desirably, (5) is the cell cultivation carrier implantable in vivo of above mentioned (4), wherein basic gas is ammonia gas. And (6) is the cell cultivation carrier implantable in vivo of above mentioned (3) has a collagen membrane to vertical direction to neutralization•gellation direction. Further, (7) is the cell cultivation carrier implantable in vivo of above mentioned (1), (2), (3), (4), (5) or (6), wherein said cell cultivation carrier implantable in vivo fills $2^{nd}$ component that promotes biochemical tissue in an independent pore. Desirably, (8) is the cell cultivation carrier implantable in vivo of above mentioned (7), wherein the $2^{nd}$ component is composed of hydroxy apatite. Further, is the cell cultivation carrier implantable in vivo, wherein the cell cultivation carrier implantable in vivo of above mentioned (6) contains an activation factor of cell. Furthermore, is the cell cultivation carrier implantable in vivo, wherein the cell cultivation carrier implantable in vivo of above mentioned (7) or (8) is contained in the $2^{nd}$ component that promotes biochemical tissue.

BRIEF ILLUSTRATION OF DRAWINGS

FIG. 1 shows a porous spongy carrier having uniform pore size and sequence obtained in Example 1 by following process. That is, ammonia gas is supplied by controlled speed from upper surface to enzyme soluble collagen (atelocollagen) solution obtained by press (max. 4 atom) filtration using membrane filter (product of Millipore Co., Ltd., pore size is 1.0 μm), by controlling neutralization•solidification.

Figure 2:
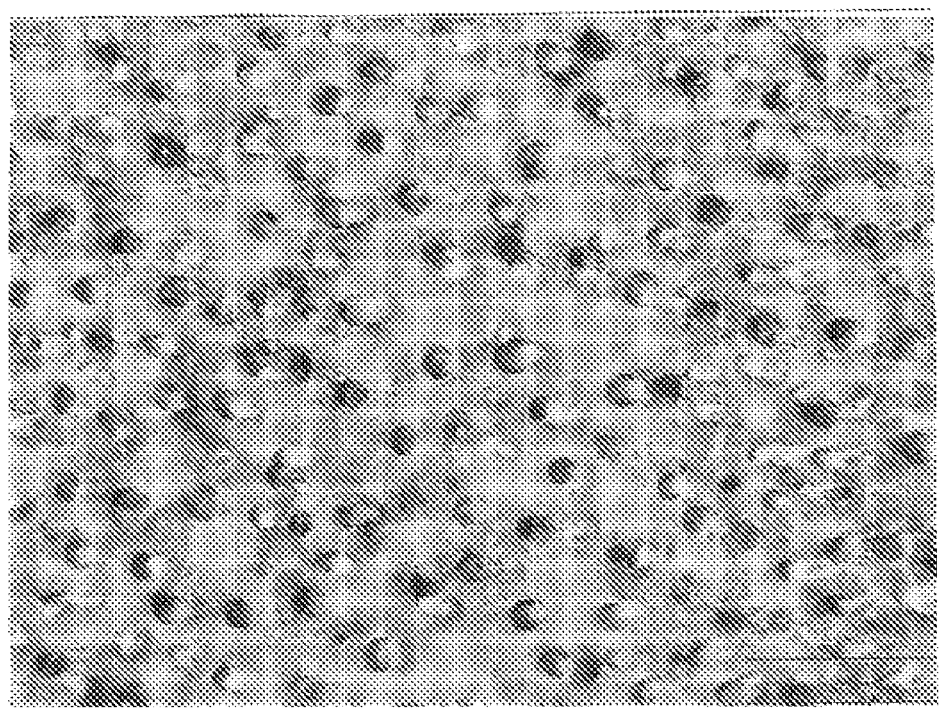

FIG. 2 shows a carrier obtained by neutralization•solidification using same process to Example 1 except omitting filtration by membrane filter (product of Millipore Co., Ltd., pore size is 1.0 μm) under pressing condition. Unevenness of pore size is large.

THE PRESENT INVENTION WILL BE ILLUSTRATED MORE IN DETAIL

A. The essential factor of the present invention is to use a product that passed through a filter of pore size of 10 μm or less and 0.2 μm or more. This factor indicates that collagen molecular, which is characterized that molecular weight is approximately 300,000, length is 300 nm, diameter is 1.5 nm and is rod shape, and since the most parts of the molecular form intermolecular crosslinking and become large protein of macro molecular weight, it can not be a solution. Therefore, for the purpose to use above mentioned collagen, it is necessary to gather a part of less intermolecular crosslinking and soluble parts at least in acid. Or, a method to cut said intermolecular crosslinking, and to extract usable parts.

Further problem is that even if the protein is seemed to form a solution, the collagen exists by crosslinking several numbers of molecular. To produce a carrier of the present invention, exist of collagen aggregation of macro molecules is not desirable. The reason why is that when such aggregation of macro molecules is contained, desired characteristics can not be obtained at neutralization•gellation process.

Accordingly, passing through process of a filter is necessary to remove such aggregation of macro molecules, and desirable pore size of the filter is 10 μm or less.

And, since the existing state of the collagen molecular depends on solution condition, it is important to restrict the filtering condition to 5-20 mg/mL concentration of collagen acidic solution and to use a filter less than 10 μm. When the concentration is high, it becomes difficult to pass through the filter even if the collagen is dispersed in molecular state, and when the concentration is low, although the macromolecular can be removed, however, removing effect is too law and causes a problem of productivity. As a pH of acidic condition, 1.5-4.5 is desirable. Kind of filter is not restricted as long as the pore size is 10 μm or less.

The used collagen is not restricted as long as it can carry out above mentioned treatment. For example, acid soluble, salt soluble or enzyme soluble type I, II or III collagen can be used, however, an enzyme soluble collagen (atelocollagen), which have especial excellent biocompatibility, is desirable. Further, regarding an origin of collagen, if the above mentioned treatment is possible, both animal originated collagen or recombinant collagen can be used.

B. As the next, collagen gel is produced by neutralizing the basic solution after said filtering treatment. As a pH of acidic solution, less than 4.5 in which collagen fibrils can be regenerated is desirable. Filtrated solution can be neutralized as is, however, said solution can be diluted or concentrated so as to change the concentration of collagen. By changing the concentration, it becomes possible to control the physical strength of finally produced carrier.

C. Neutralization can be carried out by exposing acidic solution to basic solution or basic gas, however, when concentration of collagen is changed and to avoid changing of gelling condition, it is desirable to use basic gas. Furthermore, it is desirable to carry out the neutralization to certain direction, such as from one surface to another surface. By this method, it becomes possible that the formed collagen fiber has directionality, and desirable. Specifically, in the case basic gas, neutralization progresses gradually from exposed surface to gas to another surface. Further, in the case to use basic solution, by exposing acidic solution by wrapped with an ion permeable membrane such as a permeable membrane to basic solution, neutralization can be progressed to a certain direction.

This neutralization diffusion controlling reaction by basic solution or basic gas is considered to cause organization of collagen molecule at gellation process of collagen and brings control of structure.

Said neutralization can be observed by confirming that collagen fiber is separated and whitened, or can be observed by carrying out neutralization with mixing an indicator to acidic solution of collagen.

As a basic gas, ammonia gas, methylamine or ethylamine can be mentioned. As a basic solution, alkaline aqueous solution such as aqueous solution of NaOH or buffer solution such as phosphoric acid that has pH at neutral area can be mentioned. By this neutralization, an opening of 50 μm-100 μm can be formed at the surface of structure, and the opening can be exist so that pores accumulate regularly like as honeycomb or can be exist so that pores arrange at random roughly.

Further, the pore can be penetrate from one opening of one surface to another surface, or can be a blind pore not penetrating from one surface to another surface.

Above mentioned neutralized collagen gel can be used as is for cultivation or can be used as a spongy product after freeze dried.

D. Carrier concurrently transplantation fragment of this invention is a spongy structural tissue whose starting material is collagen, and can be used by filling $2^{nd}$ component that promotes tissue regeneration in the pore. As the $2^{nd}$ component, material that is excellent in cell cytotropic ability such as chitosan, poly lactic acid or poly glycolic acid can be used, in particular, hydroxy apatite is most desirable. As a shape, besides the shape of the pore, any kinds of shape such as granule shape or film shape, which can be filled in the pore can be used, however, in particular, granule shape is desirable.

E. Further, it is possible to use the carrier by mixing a cell activation factor. Specifically, it is possible to absorb a bone forming factor by soaking the carrier into solution such as BMP or FGF, or to produce the carrier by mixing a bone forming factor to the material collagen. Furthermore, it is possible to use 2 or more cell activation factors.

According to the condition of neutralization, sometimes, a big pore is formed in a gel after neutralization and in said case it becomes hard to cultivate a cell. Therefore, it is desirable to be existent a membrane to vertical direction to neutralize direction for the purpose to protect falling down of a seeding cell. This is because pores are formed to neutralization direction, and the seeding cell is trapped by the membrane, then it becomes possible to be adhered to a wall of pore and multiplied. Specifically the membrane is separately prepared and it is possible to put it on the neutralized gel, or to put the neutralized gel on it or to put the membrane between formed gels.

F. The carrier concurrently transplantation fragment of this invention can be used after dried or by gel state as is. As a method for drying, freeze dry method is desirable. Necessary cells such as fibroblast, osteoblast, cartilage cell necessary for regenerative medicine or precursor cell of these cells are seeding to the carrier concurrently transplantation fragment, and cultivated, multiplied by ordinary method then transplanted to necessary part of a body and used.

EXAMPLES

Present invention will be illustrated in detail according to Examples. These Examples are intending to make more clearly the usefulness of this invention, and not intending to restrict the scope of this invention.

Example 1

Acidic solution of enzyme soluble collagen (atelocollagen) (concentration of collagen: 11.0 mg/mL, pH: 3.0) is filtrated by air pressure (max. 4 atoms) using a membrane filter (product of Millipore, pore size is 1 μm). Then obtained filtrated solution is neutralized and gellated. Specifically, filtrated atelocollagen solution is poured into a tray of 10 cm×10 cm size so as the height to be 1 cm. This tray is contained into a closed container (volume: 1 L) and ammonia gas flown from a bombe is inserted and filled up. After one hour, the tray is taken out. The atelocollagen solution is gellated and whitened, and water pole phase consisting of water only is formed on the gel toward from upper surface to lower surface and gel is not contained in this phase. Picture showing the surface of obtained carrier that has an opening (SEM picture by electron microscope, magnification is 4) is shown in FIG. 1.

This obtained gel is washed by water and dried by freeze dry method, thus a porous sponge having pores of one certain direction.

Comparative Example

Porous atelocollagen gel is produced by same procedure except carrying out pressing filtration using a membrane filter, and compared with the porous gel produced in Example 1.

In the gel obtained in Example 1, it is confirmed that the pore size locating of upper surface of sponge is uniform, on the contrary, in Comparative Example, unevenness of pore size is large and causes a problem at cell cultivation that needs strictly uniform pore size. Picture showing the surface of obtained carrier that has an opening of Comparative Example (SEM picture by electron microscope, magnification is 4) is shown in FIG. 2.

Example 2

By same process to Example 1 except using ammonia aqueous solution instead of ammonia gas flown from a bombe a porous sponge is produced. Obtained porous sponge has uniform pore like as Example 1.

INDUSTRIAL APPLICABILITY

By using acidic collagen solution which is characterized to be carried out above mentioned filtration, further by combining said collagen solution with specific neutralizing•gelling condition that can control the coagulation of collagen in said collagen solution, a carrier that is possible to cultivate cells suited to regenerative medicine effectively and by high concentration can be provided. Said carrier is usable in the field of regenerative medicine.

The invention claimed is:

1. A cell cultivation carrier implantable in vivo having independent pores, which have directionality in one direction, with openings of 100 μm-1000 μm on the surface thereof produced by neutralization and gelation of a collagen acidic solution, said collagen acidic solution being preliminarily prepared by passing the solution in a 5-20 mg/mL concentration of collagen through a filter of 10 μm or less in pore size.

2. The cell cultivation carrier implantable in vivo of claim 1, wherein the collagen acidic solution is neutralized to be a gel, and then freeze dried.

3. The cell cultivation carrier implantable in vivo of claim 1, wherein the directionality of the neutralization and gelation is vertical to a membrane.

4. The cell cultivation carrier implantable in vivo of claim 3, wherein the collagen acidic solution is neutralized to be a gel, and then freeze dried.

5. The cell cultivation carrier implantable in vivo of claim 1, wherein basic gas is used during said neutralization and gelation of the collagen acidic solution.

6. The cell cultivation carrier implantable in vivo of claim 5, wherein the collagen acidic solution is neutralized to be a gel, and then freeze dried.

7. The cell cultivation carrier implantable in vivo of claim 3, wherein basic gas is used during said neutralization and gelation of the collagen acidic solution.

8. The cell cultivation carrier implantable in vivo of claim 7, wherein the collagen acidic solution is neutralized to be a gel, and then freeze dried.

9. The cell cultivation carrier implantable in vivo of claim 5, wherein the basic gas is ammonia gas.

10. The cell cultivation carrier implantable in vivo of claim 9, wherein the collagen acidic solution is neutralized to be a gel, and then freeze dried.

11. The cell cultivation carrier implantable in vivo of claim 7, wherein the basic gas is ammonia gas.

12. The cell cultivation carrier implantable in vivo of claim 11, wherein the collagen acidic solution is neutralized to be a gel, and then freeze dried.

13. The cell cultivation carrier implantable in vivo of claim 3, wherein said cell cultivation carrier implantable in vivo has a collagen membrane in the vertical direction to the direction of neutralization and gelation.

14. The cell cultivation carrier implantable in vivo of claim 13, wherein basic gas is used during neutralization and gelation.

15. The cell cultivation carrier implantable in vivo of claim 14, wherein the collagen acidic solution is neutralized to be a gel, and then freeze dried.

16. The cell cultivation carrier implantable in vivo of claim 1, wherein said cell cultivation carrier implantable in vivo fills a 2nd component that promotes biochemical tissue in an independent pore.

17. The cell cultivation carrier implantable in vivo of claim 16, wherein the 2nd component is hydroxyapatite.

18. The cell cultivation carrier implantable in vivo of claim 1, wherein said cell cultivation carrier implantable in vivo contains an activation factor.

19. The cell cultivation carrier of claim 16, wherein the 2nd component is selected from the group of chitosan, polylactic acid and polyglycolic acid.

20. The cell cultivation carrier of claim 1, further comprising the step of soaking said cell cultivation carrier in a cell activation factor.

21. The cell cultivation carrier of claim 1, wherein a cell activation factor is mixed into said collagen acidic solution before passing through the filter of 10 μm or less pore size.

22. The cell cultivation carrier of claim 20, wherein said cell activation factor is Bone Morphogeneic Protein (BMP) or Fibroblast Growth Factor (FGF).

23. The cell cultivation carrier of claim 20, wherein two or more cell activation factors are used together.

* * * * *